United States Patent
Zigelman et al.

(10) Patent No.: US 10,398,337 B2
(45) Date of Patent: Sep. 3, 2019

(54) AUTOMATIC TRACKING AND ADJUSTMENT OF THE VIEW ANGLE DURING CATHETER ABLATION TREATMENT

(71) Applicant: Biosense Webster (Israel) Ltd., Yokneam (IL)

(72) Inventors: Gil Zigelman, Haifa (IL); Maxim Galkin, Haifa (IL); Ziyad Zeidan, Zemmer (IL); Hamutal Rinat Yadan, Kiryat Tivon (IL); Ehud Alkabetz, Sde Warburg (IL); Ido Ilan, Yoqneam (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 268 days.

(21) Appl. No.: 15/451,484

(22) Filed: Mar. 7, 2017

(65) Prior Publication Data
US 2018/0256055 A1    Sep. 13, 2018

(51) Int. Cl.
*A61B 5/02*    (2006.01)
*A61B 5/042*   (2006.01)
(Continued)

(52) U.S. Cl.
CPC .............. *A61B 5/0422* (2013.01); *A61B 5/06* (2013.01); *A61B 5/065* (2013.01); *A61B 5/6852* (2013.01); *A61B 5/742* (2013.01); *A61B 18/1492* (2013.01); *A61B 34/20* (2016.02); *A61B 6/12* (2013.01); *A61B 6/487* (2013.01);
(Continued)

(58) Field of Classification Search
CPC ............ A61B 18/1492; A61B 1/00183; A61B 2018/00351; A61B 2018/00577; A61B 2034/2051; A61B 34/20; A61B 5/0422; A61B 5/06; A61B 5/6852; A61B 5/742; A61B 5/02; A61B 5/042; A61B 18/14; A61B 5/00; A61B 18/00; A61B 6/00;
(Continued)

(56) References Cited

U.S. PATENT DOCUMENTS 9,220,399 B2    12/2015   Cinquin et al.
2007/0287902 A1  12/2007   Fuimaono et al.
(Continued)

FOREIGN PATENT DOCUMENTS

WO    2014118535 A2    8/2014

*Primary Examiner* — George Manuel
(74) *Attorney, Agent, or Firm* — Volpe and Koenig, P.C.

(57) ABSTRACT

A system and methods for automatically adjusting view angle when performing cardiac mapping and ablation are described herein. A three-dimensional (3D) map of a cardiac structure of a patient and a relative location (e.g., position and orientation) of a catheter within the cardiac structure may be displayed on a visual display device. According to an example procedure, the position and orientation of the tip of the catheter within the cardiac structure, and the current ablation target may be detected. A desired viewing angle of the ablation target may be known, determined, provided and/or learned through training sessions with the operator. The viewing angle of the 3D map of the cardiac structure may be automatically adjusted to correspond to the desired viewing angle using the known locations of the tip of the catheter and ablation target. Other details and procedures may be implemented, as described herein.

23 Claims, 8 Drawing Sheets

(51) Int. Cl.
*A61B 18/14* (2006.01)
*A61B 5/00* (2006.01)
*A61B 18/00* (2006.01)
*A61B 6/00* (2006.01)
*A61B 34/20* (2016.01)
*A61B 5/06* (2006.01)
*A61B 17/00* (2006.01)
*A61B 6/12* (2006.01)
*A61B 34/10* (2016.01)

(52) U.S. Cl.
CPC ............... *A61B 2017/00053* (2013.01); *A61B 2018/00351* (2013.01); *A61B 2018/00577* (2013.01); *A61B 2018/00839* (2013.01); *A61B 2034/107* (2016.02); *A61B 2034/2051* (2016.02)

(58) Field of Classification Search
CPC   A61B 2017/00053; A61B 2018/00839; A61B 5/065; A61B 6/487
See application file for complete search history.

(56) References Cited

U.S. PATENT DOCUMENTS

| | | |
|---|---|---|
| 2012/0237093 A1 | 9/2012 | Turgeman |
| 2012/0265192 A1* | 10/2012 | Sliwa .................. A61B 8/0858 606/33 |
| 2013/0172906 A1 | 7/2013 | Olson et al. |
| 2014/0180074 A1 | 6/2014 | Green et al. |

* cited by examiner

AUTOMATIC TRACKING AND ADJUSTMENT OF THE VIEW ANGLE DURING CATHETER ABLATION TREATMENT

SUMMARY

A system and methods for automatically tracking and adjusting the view angle when performing cardiac mapping and ablation are described herein. A three-dimensional (3D) map of a cardiac structure of a patient and a relative location (e.g., position and orientation) of a therapeutic catheter within the cardiac structure may be displayed on a visual display device. According to an example procedure, the position and orientation of the tip of the catheter within the cardiac structure, and the current ablation target, which may be the surface of the 3D map of the cardiac structure near the tip of the catheter, may be detected. A desired viewing angle of the ablation target may be known, determined, provided and/or learned through training sessions with the operator. The viewing angle of the 3D map of the cardiac structure may be automatically adjusted to correspond to the desired viewing angle using the known locations of the tip of the catheter and ablation target. Other details and procedures may be implemented, as described herein.

DETAILED DESCRIPTION OF THE PREFERRED EMBODIMENTS

Cardiac ablation is a medical procedure performed by electrophysiologists that may be used to correct heart rhythm defects, known as arrhythmias, by creating lesions to destroy tissue in the heart that contributes to the rhythm defects. An example arrhythmia that can be treated using cardiac ablation is atrial fibrillation, which is an abnormal heart rhythm that originates in the top chambers of the heart (i.e., the atria).

Cardiac ablation may employ long, flexible catheters that may be inserted through a small incision in groin and blood vessels to the heart, and may be used to apply energy (e.g., radio frequency (RF) energy, or extreme cold) to produce small scars or lesions to tissue to block faulty electrical impulses that may cause the heart rhythm disorders. Real-time three-dimensional (3D) imaging technology may be employed to visualize the exact position and orientation of a catheter within the heart and act as an advanced navigation system to enable the electrophysiologist to visualize and carefully guide the catheter to administer the RF energy in the appropriate locations. Goals of cardiac ablation are to remove the arrhythmia to return the patient's heart to a normal heart rhythm or reduce the frequency of arrhythmia and the severity of symptoms in the patient.

Figure 1:
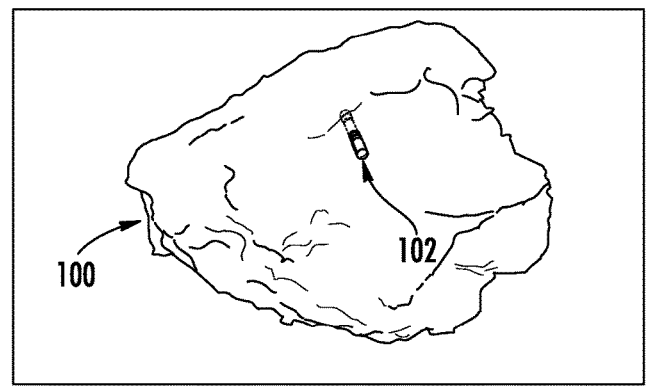
FIG. 1 shows example three-dimensional (3D) cardiac map of a patient's heart generated by a CARTO® 3 System.

An example of a real-time 3D imaging system for cardiac ablation is the CARTO® 3 System, produced by Biosense Webster®, Inc., a subsidiary of Johnson & Johnson. The CARTO® 3 System uses electromagnetic technology to create 3D maps of a patient's cardiac structure and to show the exact location and orientation of the catheters in the heart. FIG. 1 shows example 3D cardiac map of a patient's heart 100 generated by a CARTO® 3 System. The location and orientation of a catheter 102 (may be a therapeutic and/or diagnostic catheter) is illustrated within the 3D visualization of the patient's heart 100. Other objects and images, although not shown, may be included in the 3D visualization shown in FIG. 1 such as, but not limited to, the following: the location and orientation of additional catheters and devices; a 3D synthetic heart model used for orientation within the mapped heart 100; a two-dimensional (2D) image to assist in directional (e.g., up, down, back, forward) orientation; and fluoroscopy images or other background images.

Figure 2A:
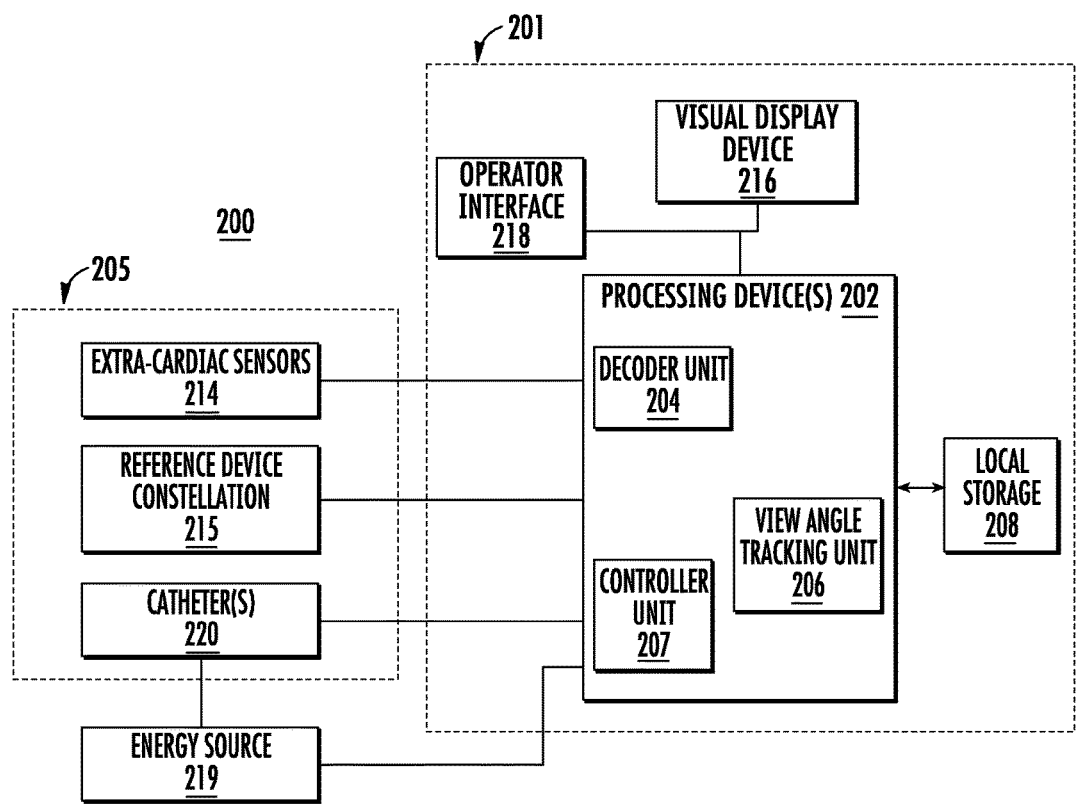
FIG. 2A is a schematic diagram of an example cardiac mapping and ablation system, in accordance with an example embodiment.

FIG. 2A is a schematic diagram of an example cardiac mapping and ablation system 200 with integrated real-time 3D imaging technology (e.g., CARTO® 3 System or other 3D imaging technology). The cardiac mapping and ablation system 200 may include, but is not limited to include, any of the following components: catheter(s) 220; extra-cardiac sensors 214; reference device constellation 215; energy source 219; and/or a console system 201. The console system 201 may include, but is not limited to include, any of the following components: processing device(s) 202; local storage 208; operator interface(s) 218; and/or visual display device 216. Certain elements of cardiac mapping and ablation system 200 may be used directly on, in, and/or in proximity to the patient 205 in order to gather information to be used for visualization and diagnostics and to perform ablation therapy. This information may be provided to the console system 201 for processing, visualization and operator control and direction, as described below.

The reference device constellation 215 may include a ring of computer-controlled (e.g., controlled by processing device(s) 202) magnets positioned beneath the patient 205. The magnets may have known and fixed strength and position values that may be used as point of origin references for the magnetic fields in the surrounding space and may provide the reference information to the processing device(s) 202 to be used in producing accurate 3D images of the heart.

The extra-cardiac sensor(s) 214 may be electrodes on the skin of a patient 205, for example. The extra-cardiac sensor(s) 214 may detect electrical activity of the heart via detection of electrical changes on the skin due to the electrophysiologic pattern of the heart, and provide information on the electrical activity to the processing device(s) 202 to be used to in diagnosing arrhythmias and determining a therapeutic course of action. Processed versions of the extra-cardiac signals detected by the extra-cardiac sensor(s) 214 may be displayed on visual display device 216.

One or more devices may be used on the patient 205 for therapeutic and diagnostic purposes. In the example cardiac mapping and ablation system 200, catheter(s) 220 are shown and described for these purposes, however, other devices may be used for diagnostics and/or therapeutic treatment.

One or more catheter(s) 220 may be percutaneously inserted by a physician through the patient's 205 vascular system into the heart of the patient 205. The catheter(s) 220 may be equipped with location and/or electrical sensors for the purpose of gathering information for diagnostic mapping and/or delivering therapeutic treatment (e.g., performing ablation). Different types of catheter(s) 220 may be used including, but not limited to, the following example types: fixed catheter; deflectable catheter; bi-directional catheter; uni-directional catheter; tricuspid mapping catheter; halo-shaped tip catheter; and/or lasso-shaped catheter. When the catheter(s) 220 is used for performing ablation on a target location (e.g., one or more locations along a path), for example by applying RF energy, the catheter(s) 220 may receive the RF energy from the energy source 219, as may be instructed by the processing device(s) 202. In an example, the catheter(s) 220 may request the RF energy directly from the energy source 219.

Figure 2B:
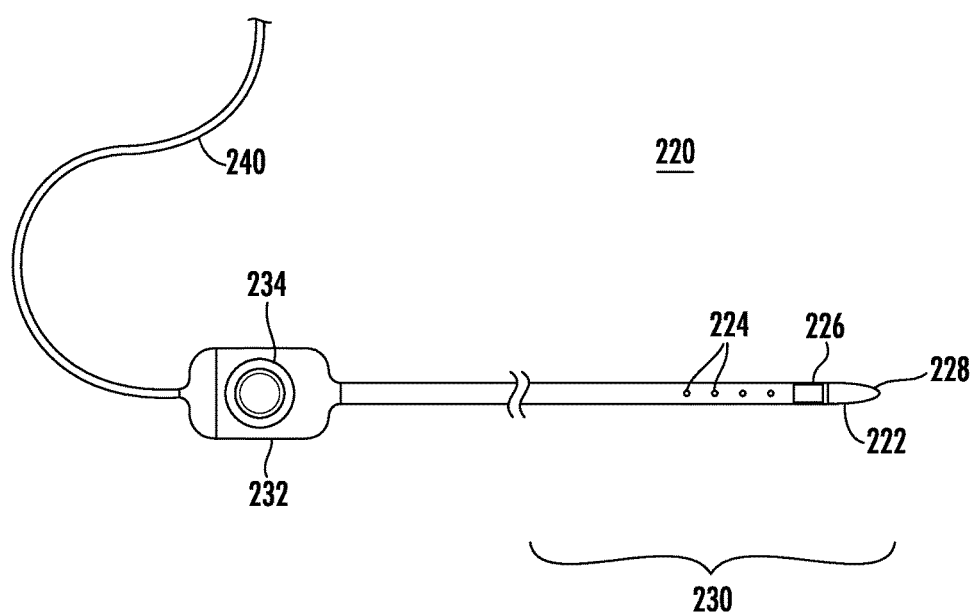
FIG. 2B is a schematic diagram of an example catheter that may be included in the example cardiac mapping and ablation system of FIG. 2A, in accordance with an example embodiment.

The catheter(s) 220 is shown in greater detail in FIG. 2B, showing some, but not all, of the elements that may be included in the catheter 220. A catheter 220 may include, but is not limited to include, any of the following components: electrode(s) 222; non-contact electrodes 224; positioning sensor(s) 226; distal tip 228; distal end 230; handle 232; and/or cable 240.

The distal end 230 of the catheter 220 may include an electrode(s) 222 at the distal tip 228 that may be used to measure electrical properties of the heart tissue. The electrode(s) 222 may also be used to send electrical signals to the heart for diagnostic purposes. The electrode(s) 222 may also perform ablation on defective cardiac tissue by applying energy (e.g., RF energy) directly to the cardiac tissue at the desired location of ablation.

The distal end 230 may include non-contact electrodes 224 arranged in an array, which may be used to simultaneously receive and measure far-field electrical signals from the walls of the heart chamber of the patient 205. The electrode(s) 222 and non-contact electrodes 224 provide information regarding the electrical properties of the heart to the processing device(s) 202 for processing.

The distal end 230 may include positioning sensor(s) 226 (also called location sensors) in the distal tip 228 of the catheter 220 that may generate signals used to determine the position and orientation of the catheter 220 in the body. In an example, the relative position and orientation of the positioning sensor(s) 226, the electrode(s) 222, and the distal tip are fixed and known in order to facilitate accurate positioning information of the distal tip. For example, the position of the positioning sensor(s) 226 may be determined in part based on the relative position to known positions outside the heart (e.g., based on extra-cardiac sensors 214). The use of positioning sensor(s) 226 may provide improved location accuracy within the magnetic fields in the surrounding space and provide location information that is adaptable to patient movement because the position information of the catheter 220 is relative to the anatomy of the patient 205.

The handle 232 of the catheter 220 may be operated by the physician and may include controls 234 to enable the physician to effectively steer the distal tip 228 in the desired direction.

The electrodes 222, 224, and sensors 226 may be connected to the processing device(s) 202 via wires that may pass through handle 232 and cable 240, in order to provide electrical and position information to the console system 201, which may be used to operate and display the function of the catheter 220 within the heart in real-time.

Within the console system 201, the processing device(s) 202 may include one or more signal processing circuits that may be contained inside a computer, for example. The processing device(s) 202 may be implemented in hardware and/or programmed in software to carry out the functions of the cardiac mapping and ablation system 200. This software may be downloaded to the processing device(s) 202 in electronic form, over a network, for example, and/or it may be provided on tangible media, such as magnetic or optical media or other nonvolatile memory. For example, enhancement may be made to the cardiac visualization and diagnostic capabilities of the cardiac mapping and ablation system 200 by downloading and installing software modules to the processing device(s) 202. In an example, processing device(s) 202 may comprise a general-purpose computer.

The processing device(s) 202 may receive, amplify, filter and/or digitize signals (carrying information or data) from catheter 220, including signals generated by positioning sensor(s) 226, tip electrode(s) 222 and/or non-contact electrodes 224. The signals are received and used by the processing device(s) 202 to compute the position and orientation of the catheter 220 as well as the electrical characteristics of the heart chamber. In an example, appropriate circuitry may be associated with the catheter 220 itself so that processing device(s) 202 receive signals that are already amplified, filtered and/or digitized.

The processing device(s) 202 may also be used to generate and send signals, containing information or instructions, to other elements in the cardiac mapping and ablation system 200. For example, the processing device(s) 202 may generate and send real-time 3D cardiac map information for display on the visual display device 216. In another example, the processing device(s) 202 may send/receive information to/from the local storage 208. In another example, the processing device(s) 202 may send signals to the catheter(2) 220 to apply RF energy provided by the energy source 219 to an ablation target.

As explained above, processing device(s) 202 may implement specific functions, which may be represented (e.g., illustratively or physically) as separate units within the processing device(s) 202. For example, the processing device(s) 202 may include a decoder unit 204 (e.g., implemented in hardware as a processing circuit and/or software as a software module) that may be configured to receive the position signals from the positioning sensor(s) 226 in the catheter 220, and may use the position signals to calculate position, orientation, temperature and/or electrocardiogram (ECG) values for the catheter tip 228.

In another example, the processing device(s) 202 may include a controller unit 207 for sending instructions to other devices in the system 200. For example, the controller unit 207 may send instructions to the energy source 219 to provide RF energy to the catheter(s) 220 for ablation, and may send instructions to the catheter(s) 220 to apply the RF energy to an ablation target (e.g., one or more locations along a path).

In another example, the processing device(s) 202 may include a view angle tracking unit 206 (e.g., implemented in hardware as processing circuits and/or software as a software module) that may be configured to automatically adjust the view angle of the ablation target, as described in detail below. The processing units 204, 207 and 206 are examples, and do not comprise all the possible functions that may be implemented in processing device(s) 202. Other processing units may be included in processing device(s) 202 but are not shown.

Visual display device 216 may be used to display 2D and/or 3D visual representations and/or maps of the heart and show the exact location and orientation of the catheter 220 within the heart, based on information processing done in the processing device(s) 202. In addition to the cardiac representations/maps and catheter(s), other objects in view and/or information (e.g., labels, diagnostics etc.) relevant to the diagnostic and therapeutic procedures may also be displayed on visual display device 216. The visual representation of the heart mapping is a critical tool used by the physician to provide an accurate and real-time visual guide for performing diagnostic and therapeutic cardiac procedures, such as cardiac ablation.

The operator interface(s) 218 may be used by one or more operators to interact with and control the cardiac mapping and ablation system 200. The operator interface(s) 218 may include, but are not limited to include, the following devices: a keyboard; and/or a mouse. The operator interface(s) 218 may allow operators to access and manipulate visual information, and may provide them with the ability to tag, or label, lesions to keep track of treatment strategies for individual patients.

Operators of the cardiac mapping and ablation system 200 may include, but are not limited to include, the following: a physician (e.g., an electrophysiologist) who may, for example, control the catheter, gather and interpret diagnostics, and perform the ablation procedure; and a Clinical Application Specialist (CAS) who functions as the physician's assistant during the procedures. Examples of the CAS' responsibilities may include, but are not limited to include, the following tasks: adjusting the 3D view of the cardiac system on the visual display device 216 to provide the physician with a better view of the ablation target; following physicians instructions; choosing pacing electrode channels; choosing connected catheters (for non-automatically detected catheters); choosing mapping catheter; setting up screen layout during case stages; acquiring points and enabling/disabling features and settings on the visual display; deleting points on the visual display; and/or correcting annotations on the visual display.

In an example, during a cardiac diagnostic or therapeutic procedure, as the physician moves the catheter within the heart, the CAS may manipulate the software (e.g., located in the processing device(s) 202) using the operator interface(s) 218 (e.g., mouse and/or keyboard) to adjust the angle of view of the 3D representation of the heart on the visual display device 216 to provide the physician with an unobstructed and direct view of the ablation target. A physician may make frequent requests to the CAS to rotate the 3D cardiac view on the visual display device 216 so that the ablation target is displayed clearly. For example, frequent view angle changes may be requested during or close to an ablation session. The efficacy and success of this approach relies heavily on the skill of the CAS and the CAS' experience and understanding of the physician's preferences for visualization during the procedures. Some amount of delay is added to the procedure each time the CAS makes a visual adjustment based on verbal instructions from the physician, which may be frequent.

In order to reduce or eliminate the physician's dependence on the CAS for ablation target view angle adjustment, approaches are described herein for automatic and real-time adjustment and rotation of the 3D view of a cardiac procedure, which may also be tailored and updated to a physician's viewing preferences. Automatic and real-time adjustment and rotation of the 3D view of a cardiac procedure may free up the CAS to perform other tasks, and may also provide different views of the ablation target at desired angles with a more seamless and continuous adjustment, thus causing less disruption and delay during an ablation procedure.

Figure 3:
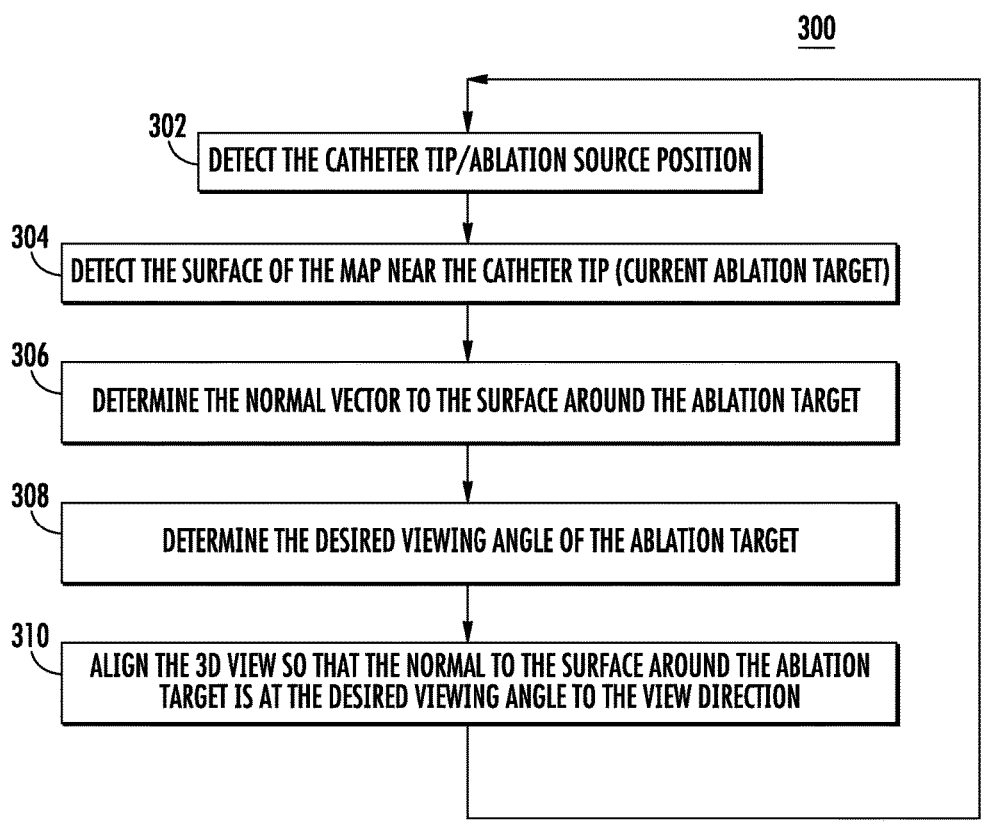
FIG. 3 shows a flow diagram of an example procedure for automatic tracking and adjustment of the view angle during cardiac ablation, in accordance with an example embodiment.

According to an embodiment, a method or procedure enables automatic tracking and adjustment of the view angle of the ablation area in a 3D visualization of a cardiac system. FIG. 3 shows a flow diagram of an example procedure 300 for automatic tracking and adjustment of the view angle during cardiac ablation.

The procedure 300 may be performed by a computer or other processing device in a cardiac mapping and ablation system, and may interact and obtain information (e.g., positioning and electrical signals) from other devices in the cardiac mapping and ablation system, as described in FIGS. 2A and 2B. For example, the procedure 300 may be implemented in the view angle tracking unit 206 (e.g., downloaded as a software module) in processing device(s) 202 in cardiac mapping and ablation system 200 shown in FIG. 2A.

With reference to FIG. 3, at step 302, the catheter tip position may be detected. The catheter tip position is the position of the source of ablation, and may be defined by the location and/or orientation of the catheter tip. As explained above with reference to FIG. 2B, the electrode(s) 222 at the distal tip 228 of the catheter 220 performs the ablation by applying energy (e.g., RF energy) to heart tissue. The catheter tip position may be determined using location information received from the catheter and reference points, as described in FIGS. 2A and 2B. Ablation occurs when the ablation source (the catheter tip) makes contact with the location of ablation.

At step 304, the surface of the 3D cardiac map near the catheter tip may be detected, which is the current ablation target or location of ablation. As explained above, ablation occurs when the ablation source (the catheter tip), makes contact with the heart tissue.

At step 306, the normal to the surface around the ablation target may be determined. The normal vector (i.e., the perpendicular vector) to the surface of the ablation target may be used in order to adjust the viewing angle with respect to the ablation target. For example, the normal vector may be defined in three-dimensions using the x, y and z Cartesian coordinates. The normal vector may be determined using detailed position information regarding the heart tissue around the tip of the catheter using the same position information used to generate the 3D cardiac maps as received from sensors in and around the patient (e.g., see description of FIGS. 2A and 2B).

Figure 4:
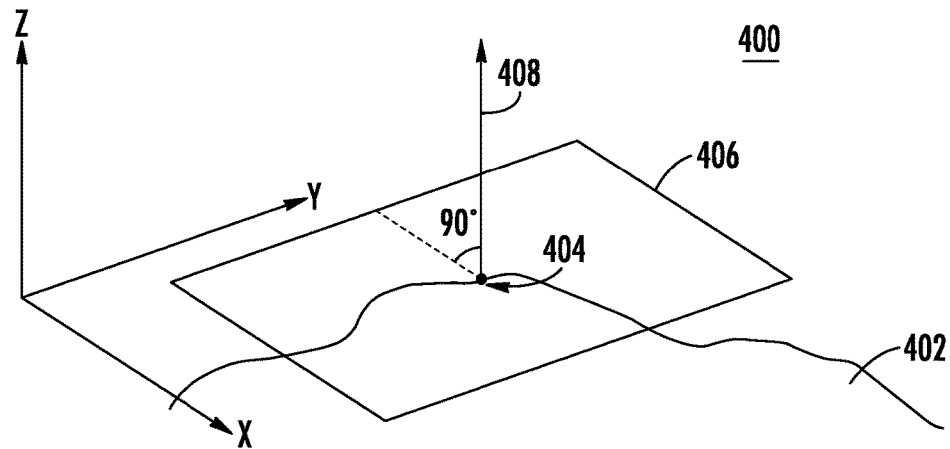
FIG. 4 shows a 3D graphical representation of a normal vector to the surface around the ablation target, in accordance with an example embodiment.

FIG. 4 shows a 3D graphical representation 400 of a normal vector 408 to the surface 406 around the ablation target 404. The ablation target 404 is the point where the tip of the catheter makes contact with the cardiac tissue 402. The surface 406 around the ablation target 404 is the two-dimensional (2D) surface 406 (e.g., in the x-y plane) that makes contact exactly at the ablation target 404. Then, the normal vector 408 may be determined to be the vector at a 90° (i.e., perpendicular) angle relative to the 2D surface 406 at the ablation target 404. The normal vector 408 may be used to adjust the viewing angle to the desired viewing angle, as described in steps 308 and 310 below. Note that although a normal vector 408 is described herein, a vector at any other angle may be used similarly for the purpose of adjusting the viewing angle.

At step 308, the desired viewing angle with respect to the surface around the current ablation target may be determined. For example, a physician may have a preferred viewing angle of the ablation target when performing an ablation procedure when viewing the ablation procedure on the visual display. In this case, the preferred viewing angle may be provided or entered to the system by an operator. For example, with reference to FIG. 2A, a physician (or CAS) may use operator interface(s) 218 to provide one or more viewing angles to processing device(s) 202 to be used by the view angle tracking unit 206. The viewing angles may be stored in console system 201 in local storage 208, for example.

In an example, multiple viewing angles may be provided by an operator, and may be associated with different anatomical regions. For example, a physician may desire a first viewing angle when in a first chamber of the heart, and a second viewing angle (different from the first viewing angle) when in a second chamber of the heart, and so on and so forth. For example, the automatic view strategy may be different for the left pulmonary veins (LPV) than for the right pulmonary veins (RPV). Viewing angle preferences may be stored in association with a particular physician (e.g., in local storage 208 in FIG. 2A), such that the procedure 300 may support use by multiple operators/physician, each with customized preferences.

If a preferred viewing angle is not known, a default viewing angle may be used. For example, a default angle may be a perpendicular angle, such that the viewing angle is perpendicular to the surface around the ablation target. In an example, the procedure 300 may commence with a default or entered viewing angle, and may adapt or learn the preferred viewing angle(s) associated with a particular physician during procedures performed by the physician. For example, training sessions may be performed so that the system (e.g., view angle tracking unit 206 in FIG. 2A) may learn the view preferences of the physician during the ablation sessions (e.g., using a machine learning approach). The learned preferences may be stored and automatically applied to future ablation procedures performed by the physician. Thus, the system (e.g., view angle tracking unit 206 and/or processing device(s) 202 in FIG. 2A) may be in a "learning" mode for several procedures performed by the physician, in order to determine the physician's preferences. Once recorded, these different preferences may be implemented, as appropriate, during different parts of the procedure 300. This learning mode may be stopped after a set number of procedures, or it may be continually updated as the system is used for more procedures.

At step 310, the view of the ablation target, within the 3D map of the cardiac system, may be automatically aligned so that the normal of the view of the surface around the ablation target is at the desired viewing angle to the view direction. Thus, in step 310 the information gathered in steps 302-308 may be used (e.g., by the view angle tracking unit 206 in FIG. 2A), to adjust the alignment of the view to the desired viewing angle, such that the view angle adjustment may be automatically displayed on the visual display. The view may include the 3D map of the heart, but may also include other maps and objects in the view such as catheters and cables, all with relative positions and orientations to each other. Thus, adjusting the alignment of the 3D view to the desired angle includes adjusting the angle of view of for all maps, surfaces and objects in the 3D view while maintaining the same relative positions and orientations. In other words, for objects and maps that share the same coordinate system, if the coordinate system is rotated in the view, then all objects may be similarly rotated in the view together, thus maintaining their relative position and orientation. The adjusting or rotation of the viewing angle may also take into account the movement or change of location and orientation of objects during the procedure.

Figure 5:
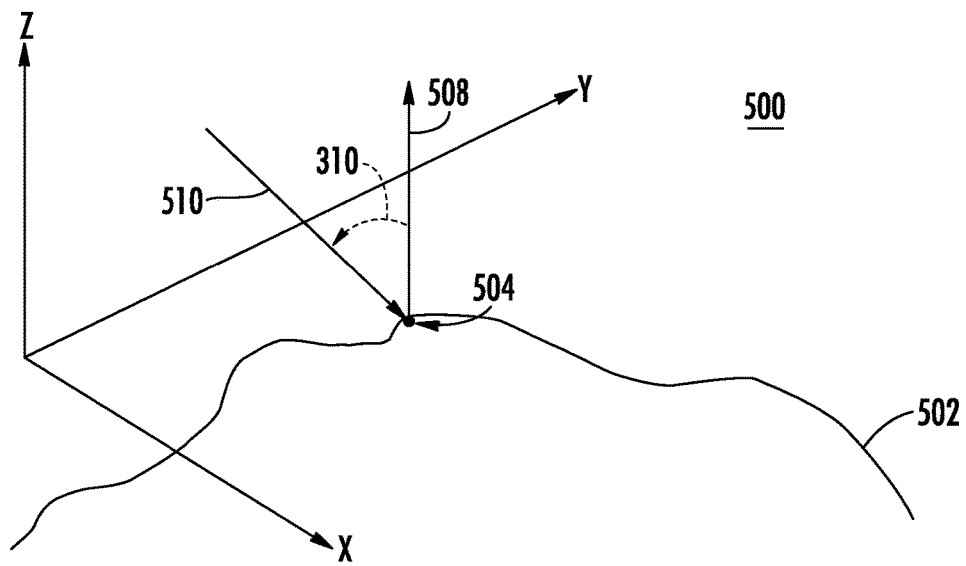
FIG. 5 shows a 3D graphical representation of a normal vector with automatic alignment to a desired viewing angle, in accordance with an example embodiment.

FIG. 5 shows a 3D graphical representation 500 of a normal vector 508 with automatic alignment step 310 to a desired viewing angle 510. The normal vector 508 at the ablation target 504 on the cardiac tissue 502 is adjusted to line up with the desired viewing angle 510. Because the visualization is three-dimensional, the normal vector 508 is adjusted in the 3D space along the x, y and z axes to correspond to the desired viewing angle 510.

The procedure 300 may be repeated throughout an ablation procedure, and for different mapping locations or ablation target locations, for example as a catheter moves along a pathway within a cardiac structure. Moreover, the procedure 300 may be adapted by allowing operators to input information, such as viewing angle preferences, before, during and/or after an ablation procedure in order to customize and optimize the effectiveness of the procedure 300 for any particular physician. Moreover, the steps 302-310 may be performed in any order.

In an example, an operator may selectively activate and/or deactivate procedure 300 when operating an ablation system, allowing a physician to switch between automated view angle tracking, and manual view angle adjustment by a CAS.

In contrast to systems that require a CAS to change the view displayed during an ablation procedure, procedure 300 enables automatic tracking of the view angle while ablating and automatic and real-time adjustment of the view angle in accordance with a physician's preference. The automated procedure 300 may provide the physician with improved focus on the ablation procedure without having to be concerned with view angle adjustment, and may free up the CAS to perform other tasks.

Figure 6A:
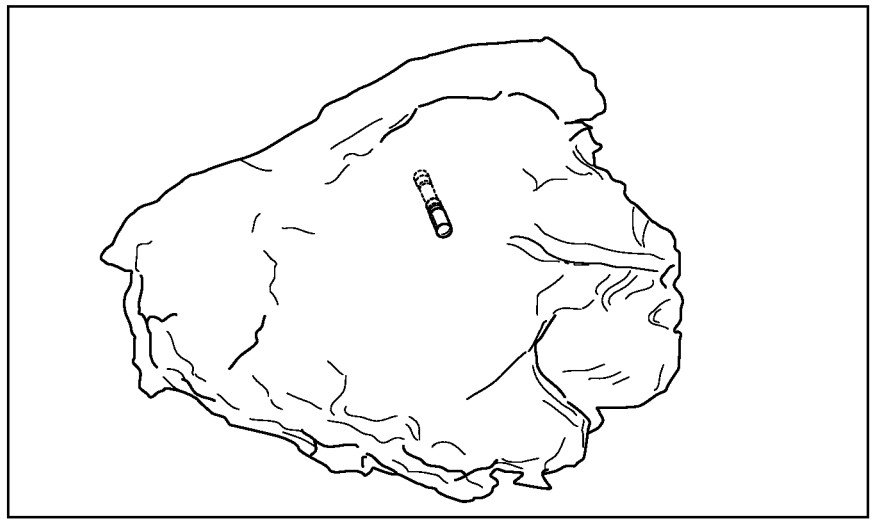
FIGS. 6A-6G show example 3D cardiac images generated along an ablation line and showing the relative positions and orientations of a catheter in an atria chamber at various angles during a cardiac mapping and ablation procedure.
Figure 6B:
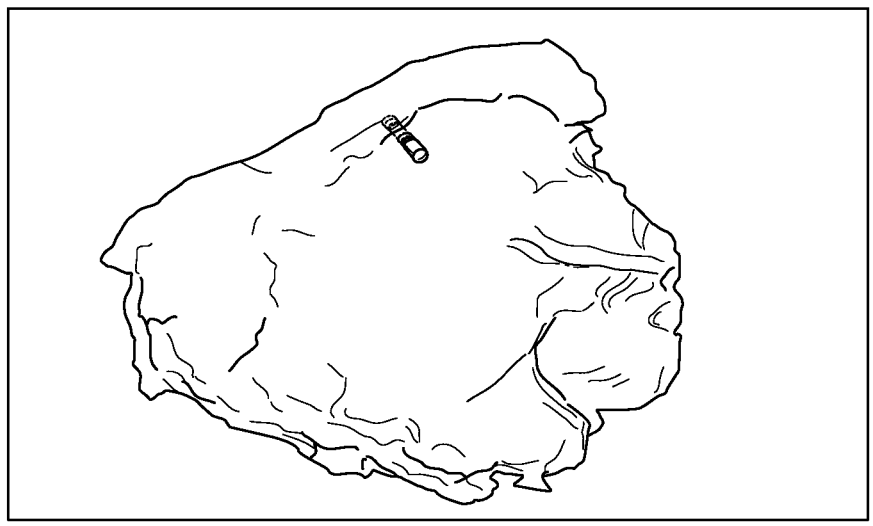
Figure 6C:
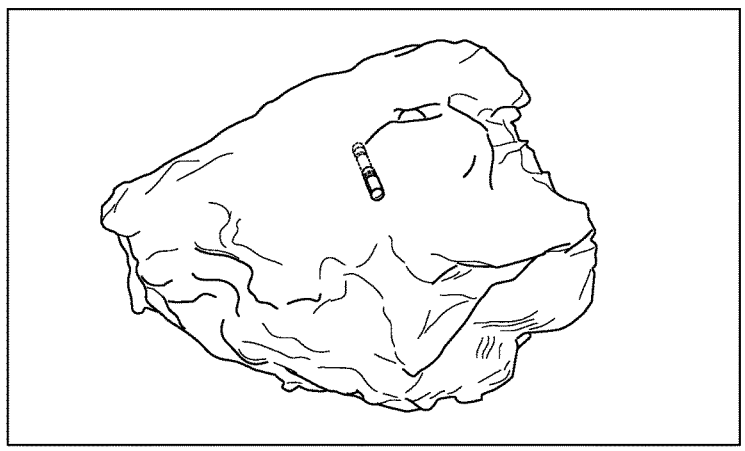
Figure 6D:
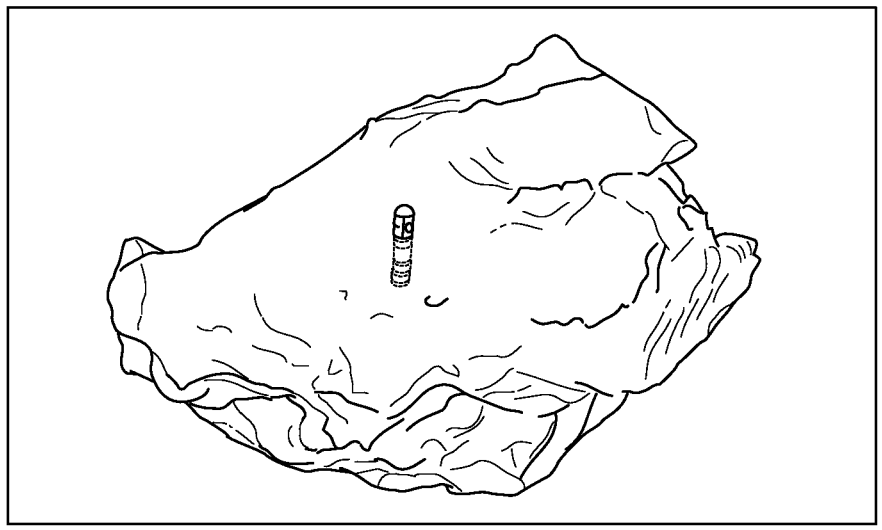
Figure 6E:
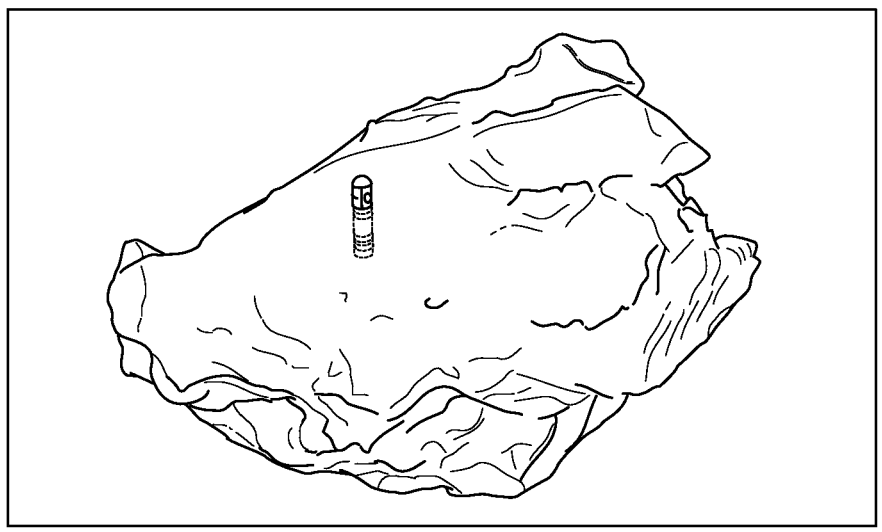
Figure 6F:
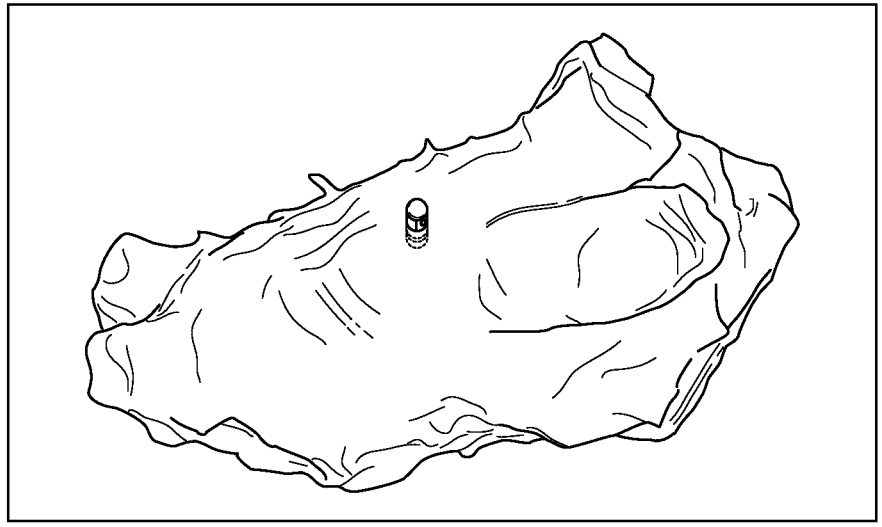
Figure 6G:
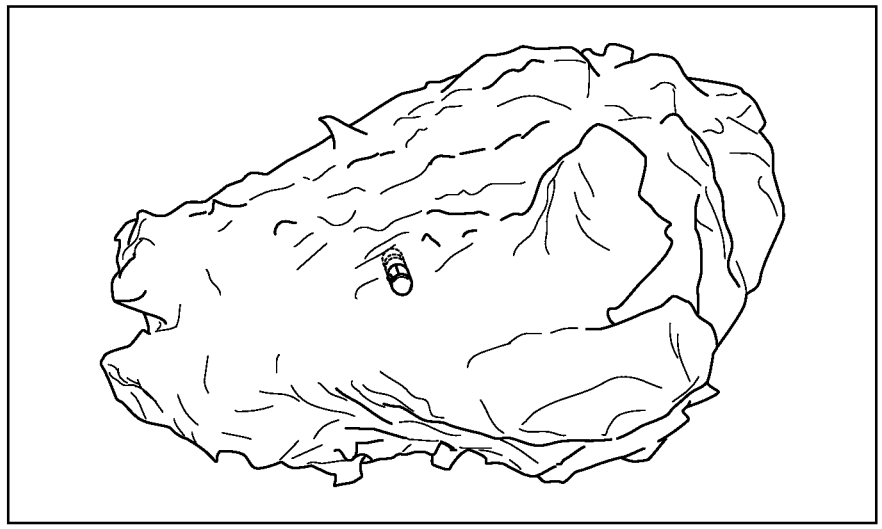

FIGS. 6A-6G show example 3D cardiac images generated along an ablation line (not shown) and showing the relative positions and orientations of a catheter in an atria chamber at various angles during a cardiac mapping and ablation procedure. The path of the catheter in FIGS. 6A-6G starts at the anterior wall of the atria chamber (FIG. 6A), moves towards the roof of the atria chamber (FIGS. 6B-6E), and continues toward the posterior wall of the atria chamber (FIGS. 6F and 6G). The pathway of ablation in FIGS. 6A-6G is an example pathway that may be used to achieve pulmonary vein isolation (PVI) ablation to treat atrial fibrillation. FIGS. 6A-6G illustrate how a procedure for automatic tracking and adjustment of the view angle during cardiac ablation (such as procedure 300 in FIG. 3) can be used to adjust the viewing angle of the catheter and 3D cardiac image to a desirable viewing angle for the physician performing the ablation operation.

FIG. 6A shows a first view of the catheter at a first ablation position along a path of the ablation line. FIG. 6B shows a first view of the catheter at a second ablation position along the ablation pathway. The viewing angle of the 3D image is the same in FIGS. 6A and 6B, however, the view angle is not optimal for the second catheter ablation position shown in FIG. 6B. FIG. 6C shows a second viewing angle of the second ablation position along the ablation pathway that is an optimized or improved viewing angle of the second ablation position, such that the second viewing angle may be determined using automatic tracking and adjustment of the view angle during cardiac ablation, as described herein. As explained above, this optimized viewing angle may be based on the physician's preferences, some default value, or learned viewing angle.

FIGS. 6D through 6G show third, fourth, fifth, and sixth catheter positions along the ablation line, respectively, with an desired viewing angle of the ablation region and target for each respective position, as may be achieved using automatic tracking and adjustment of the view angle during cardiac ablation.

The embodiments and procedures described herein may be implemented in hardware, and/or software. A computer system for performing ablation may be capable of running software modules that introduce additional features including the procedures described herein. The procedures described herein may enable advanced cardiac visualization, and diagnostic capabilities to enhance clinicians' ability to diagnose and treat heart rhythm disorders. Although the procedures disclosed herein are describe with respect to ablation procedures within the heart, the procedures may be similarly used for ablation in other parts of the body.

What is claimed is:

1. A system for performing cardiac mapping and ablation, the system comprising:
    a processing device configured to generate a three-dimensional (3D) map of a cardiac structure of a patient and a relative location of a catheter within the cardiac structure and provide the 3D map and relative location of the catheter to a visual display device;
    the visual display device configured to visually display the 3D map of the cardiac structure and the relative location of the catheter within the cardiac structure, wherein the 3D map of the cardiac structure is displayed at a viewing angle;
    the processing device configured to detect a position and orientation of a tip of the catheter within the cardiac structure;
    the processing device configured to determine a surface of the 3D map of the cardiac structure near the tip of the catheter, wherein the surface of the 3D map of the cardiac structure near the tip of the catheter is an ablation target or mapping location;
    the processing device configured to determine a desired viewing angle of the ablation target or mapping location;
    the processing device configured to automatically adjust the viewing angle of the 3D map of the cardiac structure and the relative location of the catheter within the cardiac structure based on the desired viewing angle and provide the adjusted viewing angle to the visual display device; and
    the visual display device configured to update the viewing angle of the 3D map of the cardiac structure and the relative location of the catheter within the cardiac structure to the adjusted viewing angle.

2. The system of claim 1, wherein:
    the processing device is further configured to determine a normal vector to the surface of the 3D map of the cardiac structure near the tip of the catheter, and
    wherein the processing device is configured to adjust the viewing angle of the 3D map of the cardiac structure by aligning the normal vector to the surface of the 3D map of the cardiac structure with the desired viewing angle.

3. The system of claim 1, wherein the desired viewing angle is a default viewing angle stored in a local storage.

4. The system of claim 3, wherein the default viewing angle is a perpendicular angle or a constant predefined offset from the perpendicular angle.

5. The system of claim 1, wherein:
    the processing device is further configured to receive the desired viewing angle of the ablation target or mapping location from an operator and store the desired viewing angle in a local storage.

6. The system of claim 1, wherein:
    the processing device is further configured to receive a plurality of desired viewing angles of the ablation target or mapping location associated with a corresponding plurality of anatomical regions within the cardiac structure, and store the plurality of desired viewing angles in local storage.

7. The system of claim 1, wherein:
    the processing device is configured to determine the desired viewing angle of the ablation target or mapping location by performing a series of training sessions to learn viewing preferences of a physician, and store the desired viewing angle in a local storage.

8. The system of claim 1, wherein:
    the processing device is configured to detect the position and orientation of the tip of the catheter within the cardiac structure using position information received from positioning sensors located in the catheter.

9. The system of claim 1, wherein:
    the processing device is configured to adjust the viewing angle of the 3D map of the cardiac structure and the relative location of the catheter within the cardiac structure based on the desired viewing angle continuously and in real-time as the position and the orientation of the tip of the catheter within the cardiac structure.

10. The system of claim 1, wherein:
    the processing device is further configured to receive instructions from an operator to enable or disable automatic adjusting of the viewing angle of the 3D map of the cardiac structure.

11. The system of claim 1, wherein:
    the visual display device is further configured to visually display a plurality of maps of the cardiac structure and a plurality of objects within or around the cardiac structure with constant relative position and orientation to each other, wherein the plurality of maps of the cardiac structure includes the 3D map of the cardiac structure and the plurality of objects within or around the cardiac structure include the catheter; and
    the visual display device is further configured to update the viewing angle of the plurality of maps of the cardiac structure and the plurality of objects within or around the cardiac structure to the adjusted viewing angle, while maintaining the constant relative position and orientation to each other.

12. A method for automatically tracking and adjusting a view angle as part of a cardiac mapping and ablation procedure, the method comprising:
    generating a three-dimensional (3D) map of a cardiac structure of a patient and a relative location of a catheter within the cardiac structure and provide the 3D map and relative location of the catheter to a visual display device;
    visually displaying the 3D map of the cardiac structure and the relative location of the catheter within the cardiac structure, wherein the 3D map of the cardiac structure is displayed at a viewing angle;
    detecting a position and orientation of a tip of the catheter within the cardiac structure;
    determining a surface of the 3D map of the cardiac structure near the tip of the catheter, wherein the surface of the 3D map of the cardiac structure near the tip of the catheter is an ablation target or mapping location;

determining a desired viewing angle of the ablation target or mapping location;

automatically adjusting the viewing angle of the 3D map of the cardiac structure and the relative location of the catheter within the cardiac structure based on the desired viewing angle and provide the adjusted viewing angle to the visual display device; and updating the viewing angle of the 3D map of the cardiac structure and the relative location of the catheter within the cardiac structure to the adjusted viewing angle.

13. The method of claim 12, further comprising:

determining a normal vector to the surface of the 3D map of the cardiac structure near the tip of the catheter, and wherein the adjusting the viewing angle of the 3D map of the cardiac structure includes aligning the normal vector to the surface of the 3D map of the cardiac structure with the desired viewing angle.

14. The method of claim 12, wherein the desired viewing angle is a default viewing angle stored in a local storage.

15. The method of claim 14, wherein the default viewing angle is a perpendicular angle or a constant predefined offset from the perpendicular angle.

16. The method of claim 12, further comprising:

receiving the desired viewing angle of the ablation target or mapping location from an operator and store the desired viewing angle in a local storage.

17. The method of claim 12, further comprising:

receiving a plurality of desired viewing angles of the ablation target or mapping location associated with a corresponding plurality of anatomical regions within the cardiac structure, and storing the plurality of desired viewing angles in local storage.

18. The method of claim 12, wherein the determining the desired viewing angle of the ablation target or mapping location includes performing a series of training sessions to learn viewing preferences of a physician, and storing the desired viewing angle in a local storage.

19. The method of claim 12, wherein the detecting the position and orientation of the tip of the catheter within the cardiac structure uses information received from positioning sensors located in the catheter.

20. The method of claim 12, wherein the adjusting the viewing angle of the 3D map of the cardiac structure and the relative location of the catheter within the cardiac structure based on the desired viewing angle is done continuously and in real-time.

21. The method of claim 12, further comprising:

receiving instructions from an operator to enable or disable automatic adjusting of the viewing angle of the 3D map of the cardiac structure.

22. The method of claim 12, further comprising:

visually displaying a plurality of maps of the cardiac structure and a plurality of objects within or around the cardiac structure with constant relative position and orientation to each other, wherein the plurality of maps of the cardiac structure includes the 3D map of the cardiac structure and the plurality of objects within or around the cardiac structure include the catheter; and updating the viewing angle of the plurality of maps of the cardiac structure and the plurality of objects within or around the cardiac structure to the adjusted viewing angle, while maintaining the constant relative position and orientation to each other.

23. The method of claim 12, wherein the catheter includes a plurality of positions sensors and wherein the method is performed for a plurality of ablation targets or mapping locations.

* * * * *